United States Patent [19]
Boquet

[11] Patent Number: 5,482,613
[45] Date of Patent: Jan. 9, 1996

[54] METHOD AND APPARATUS FOR MAKING A GEL PLATE WITH A POROUS MEMBRANE FOR SEPARATING AND TRANSFERRING MACROMOLECULES BY ELECTROPHORESIS

[75] Inventor: Jean Boquet, Le-Perray-en-Yvelines, France

[73] Assignee: Bertin & Cie, Plaisir, France

[21] Appl. No.: 244,528

[22] PCT Filed: Oct. 5, 1993

[86] PCT No.: PCT/FR93/00982

§ 371 Date: May 31, 1994

§ 102(e) Date: May 31, 1994

[87] PCT Pub. No.: WO94/08701

PCT Pub. Date: Apr. 28, 1994

[30] Foreign Application Priority Data

Oct. 9, 1992 [FR] France ..................................... 92 12004

[51] Int. Cl.⁶ ........................................................ C25B 9/00
[52] U.S. Cl. .................................. 204/299 R; 204/182.8; 264/259
[58] Field of Search ............................ 204/182.8, 299 R; 264/259

[56] References Cited

U.S. PATENT DOCUMENTS 5,293,703  3/1994  Coste et al. .......................... 204/180.1
5,344,543  9/1994  Boquet ................................. 204/299 R

FOREIGN PATENT DOCUMENTS 0490729  6/1992  European Pat. Off. .
0499546  8/1992  European Pat. Off. .

*Primary Examiner*—John Niebling
*Assistant Examiner*—C. Delacroix-Muirheid
*Attorney, Agent, or Firm*—Bell, Seltzer, Park & Gibson

[57] ABSTRACT

The invention concerns a method of making a gel plate with a microporous membrane by means of a cassette comprising a rectangular frame and a removable bottom plate, means for tensioning a membrane disposed on the frame substantially uniformly, and means for pouring liquid gel into the frame between the tensioned membrane and the removable bottom plate which also carries a comb for forming wells in the gel plate for receiving samples of macromolecules.

The invention makes it quick and easy to manufacture gel plates with a microporous membrane for separation and transfer of macromolecules by electrophoresis.

6 Claims, 3 Drawing Sheets

METHOD AND APPARATUS FOR MAKING A GEL PLATE WITH A POROUS MEMBRANE FOR SEPARATING AND TRANSFERRING MACROMOLECULES BY ELECTROPHORESIS

BACKGROUND OF THE INVENTION

This invention concerns a method and apparatus for making a gel plate with a microporous membrane for separating and transferring macromolecules by electrophoresis, the method and the apparatus utilizing a cassette with a rectangular frame and a removable bottom plate and into which the gel is poured in liquid form.

The applicant has already proposed a method and a manufacturing apparatus of that type, described in International Patent Application WO 93/01491, in which the gel in liquid form is first poured into the cassette until it is level with the top edge of the rectangular frame, after which a dry microporous membrane is laid progressively on to the gel and the frame, traction is applied to the periphery of the membrane to tension it in substantially uniform manner, and the gel is allowed to solidify while keeping the membrane tensioned.

That method and apparatus allow gel plates to be made with one face covered by an adhering microporous membrane, generally of nitrocellulose or nylon, satisfying a number of criteria, such as the homogeneity of the gel, uniformity of its thickness, absence of air bubbles between the gel and the membrane, flatness of the membrane and cleanness of its free face.

That method and apparatus also make it possible to avoid some problems with the prior art, such as the gel overflowing onto the free face of the membrane and the formation of folds in the membrane, resulting from its elongation during its impregnation by the gel, which problems are generally encountered when the liquid gel is poured onto the membrane placed on a support.

SUMMARY OF THE INVENTION

The present invention concerns improvements in the method and the apparatus described in the cited prior application of the applicant, these improvements making it possible to simplify and make easier the manufacture of a gel plate with a microporous membrane.

The invention thus provides a method of making a gel plate with a microporous membrane for separating and transferring macromolecules by electrophoresis, the gel being poured in liquid form into a cassette comprising a rectangular frame and a removable bottom plate, the method being characterized in that it consists in

- firstly placing a dry microporous membrane on the rectangular frame and putting this membrane under tension in substantially uniform manner by exerting traction forces on the edges of the membrane,

- then pouring the liquid gel into the cassette under the membrane, until it fills the space defined in the frame by the tensioned membrane and the bottom plate,

- and allowing the gel to solidify while keeping the membrane under tension.

The method according to the invention has the advantage that the microporous membrane is placed on the rectangular frame and put under tension before the liquid gel is poured in, which is much simpler and easier to perform than is laying a microporous membrane progressively onto a layer of liquid gel filling a cassette.

According to another characteristic of the invention, the method also consists in pouring the gel into the cassette via one end thereof, this end being opposite to the end having a comb on the bottom plate for forming wells in the gel plate for receiving samples of macromolecules.

The end of the cassette used for pouring in the gel is advantageously raised slightly, which allows the air contained between the bottom plate and the membrane to be expelled progressively as the gel is poured, in order to guarantee that there are no bubbles of air between the gel and the membrane.

The traction forces are preferably applied continuously to two opposite edges of the membrane in directions radiating from a fixed point located on a median axis of the membrane, for example in the vicinity of a transverse edge thereof.

In order to facilitate the tensioning of the membrane, the method according to the invention consists initially in fixing two extensible longitudinal strips on the two said edges of the membrane, for example by an adhesive, and in exerting the aforesaid traction forces on the membrane by means of pushers engaged in holes in the said strips and urged resiliently outwards by springs, the pushers and the springs being fitted in guide grooves formed in the corresponding sides of the frame.

While the gel is being poured, the traction exerted continuously on the edges of the membrane serves, in particular, to take up elongation of the membrane resulting from the membrane being impregnated by the liquid gel and ensures flatness of the membrane.

The invention also provides apparatus for making a gel plate with a microporous membrane for separation and transfer of macromolecules by electrophoresis, the apparatus comprising a cassette formed by a rectangular frame and a removable bottom plate, and pouring means for pouring liquid gel into the interior of the cassette onto the bottom plate, the apparatus being characterized in that two opposite longitudinal sides of the cassette comprise traction means which cooperate with two opposite longitudinal edges of the membrane for placing the latter under tension in substantially uniform manner, before pouring in the gel, and in that the pouring means are mounted at one end of the cassette and comprise a channel for the gel opening into the cassette between the bottom plate and the membrane tensioned over the frame.

The said traction means comprise pushers guided in grooves in the aforesaid sides of the frame and urged towards the outside by springs, the pushers including means for gripping the edges of the membrane.

The apparatus advantageously also comprises means acting on the pushers for shifting them towards the interior of the frame, against the action of the springs, into a position allowing a non-tensioned membrane to be placed on the cassette, and the engagement of this membrane on the pushers.

In a preferred embodiment, the apparatus comprises a table supporting and positioning the cassette and two movable arms mounted on the table on either side of the cassette and carrying fingers adapted to be engaged in the guide grooves of the pushers, these arms being movable between an active position in which the fingers are engaged in the guide grooves of the pushers and push them towards the interior of the cassette, and an inactive position in which the fingers are retracted from the guide grooves of the pushers.

These means facilitate placement of a membrane and its attachment to the traction means provided on the frame of a cassette. The two movable arms thus allow all of the traction means to be put simultaneously in predetermined positions for reception of a membrane.

According to yet another characteristic of the invention, the pouring means for the gel comprise a tank carried by a support plate for sealed introduction into one open end of the frame, the tank comprising a cylindrical bottom part mounted to rotate in a cylindrical seat of the support plate and formed with an outlet channel for the gel adapted to be placed by rotation in communication with a duct in the support plate, the ends of the duct opening respectively into the said cylindrical seat and the interior of the frame between the bottom plate and the tensioned membrane.

This tank allows the amount of gel needed for the manufacture of a gel plate firstly to be measured out and then, by rotation on the support plate, it allows this measured amount to flow out into the cassette.

The structure of these pouring means also makes it possible to effect automatic de-gassing of the gel and evacuation of the air contained in the outlet channel from the tank, before the gel is poured.

Generally speaking the method and the apparatus according to the invention greatly facilitate the manufacture of a gel plate with a microporous membrane, such that this manufacture can be effected at a high rate by non-specialist personnel, the gel plates made in this way having homogenous and reproducible properties.

The invention will be better understood and other characteristics, details and advantages thereof will appear more clearly from a reading of the description which follows, given by way of example, with reference to the accompanying drawings, in which:

DETAILED DESCRIPTION OF THE DRAWINGS

Figure 1:
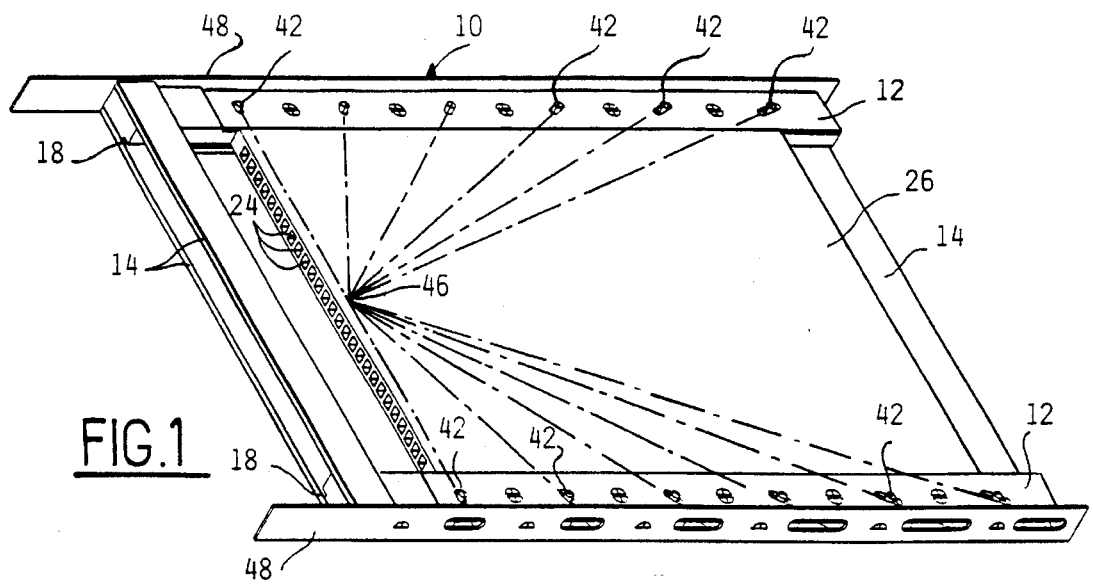
FIG. 1 is a diagrammatic perspective view of a gel plate made in a cassette in accordance with the invention, the microporous membrane being removed for clarity.
Figure 2:
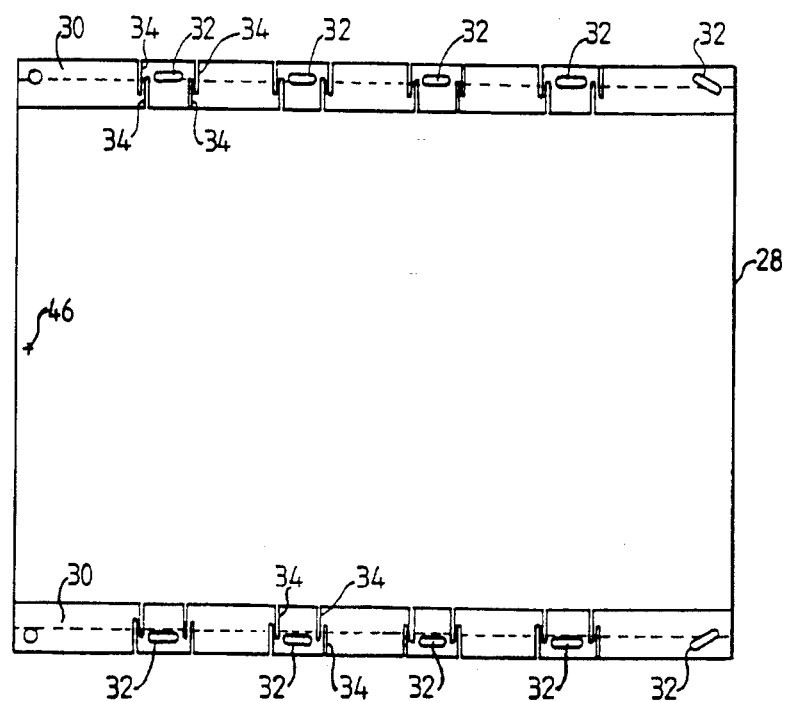
FIG. 2 is a diagrammatic plan view of the microporous membrane.

Reference is made first of all to FIGS. 1 and 2, which respectively show a gel plate made in a cassette in accordance with the invention and the microporous membrane associated with this gel plate.

Like the cassette of the aforesaid International Application WO 93/01491, the contents of which are incorporated by reference, the cassette of FIG. 1 comprises a rectangular frame 10 formed by two longitudinal rails 12 connected together at their ends by transverse bars 14, and a removable bottom plate 16, (shown diagrammatically in FIG. 6), which is guided in grooves 18 in the inside faces of the longitudinal rails 12 and which is fitted at one of its ends with a comb 20 having a row of teeth 22 adapted to form wells 24 in the gel plate 26 manufactured by means of the cassette, the bottom plate 16 being withdrawn from the cassette when the gel plate 26 is used to separate and transfer macromolecules by electrophoresis.

The microporous membrane 28 associated with the gel plate 26 is shown in FIG. 2 and is formed by a very thin film having a thickness in the order of 0.15 mm for example, a width of 170 mm and a length of 225 mm in one specific embodiment. The two longitudinal edges of the membrane are fixed, for example by adhesive or by welding, to two strips 30 of plastics material, having a thickness of the order of a millimeter for example and a width around 15 mm in one specific embodiment, and which include firstly elongate holes 32 for engagement on tensioning means for the membrane and secondly transverse slots 34 opening alternately to one edge and to the other edge of the strip 30 to allow longitudinal extension thereof.

Figure 3:
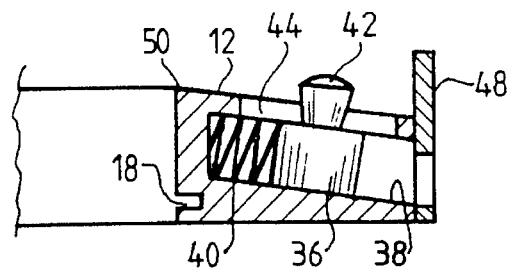
FIG. 3 is a fragmentary view in section and to a larger scale of traction means for a microporous membrane.

The tensioning means for the membrane 28 are provided in the longitudinal rails 12 of the frame 10, and as is best seen in the enlarged view in section of FIG. 3, they comprise pushers 36 guided in the grooves 38 of the rails 12 and springs 40 fitted in the grooves between the bottoms thereof and the pushers 36 to urge them resiliently towards the outside of the frame 10. Each pusher 36 includes a lug 42 on its top face fitting through an elongate aperture 44 of the top face of the corresponding rail 12 and adapted to be engaged in a hole 32 of a strip 30 of the membrane, so as to engage the membrane on the tensioning means.

The grooves 38 and the elongate apertures 44 of the rails 12 are orientated so as to radiate away from a fixed point 46 which is located on the longitudinal median axis of the gel plate 26 and of the membrane 28, in the immediate vicinity of the edge of the gel plate having the wells 24.

The guide grooves 38 for the pushers 36 open to the outside of the rails 12 into apertures formed in two side strips 48 which are fixed on the outer faces of the rails 12.

As seen in the enlarged view of FIG. 3, the top faces of the rails 12 are transversely inclined downwardly towards the outside, as are the guide grooves 38 for the pushers 36, in such a manner that the membrane 28 can be applied on the crests formed by the inside longitudinal edges 50 of the rails 12.

In order to make a gel plate in conformity with the invention, the procedure is as follows:

Firstly, a microporous membrane 28 is made, to the longitudinal edges of which are fixed the strips 30, by adhesive or by welding, the longitudinal edges of the membrane extending approximately along the central axes of the strips 30 so as to leave the holes 32 thereof free.

The membrane prepared in this way is then placed on the top face of the frame 10 fitted with the bottom plate 16. The lugs 42 of the pushers 36 are engaged in the holes 32 of the strips 30 of the membrane, which is then put under substantially uniform tension by the springs 40 urging the pushers 36 resiliently outwards. The elongation of the membrane is in the order of one percent.

Under these conditions, the membrane, together with the frame 10 and the bottom plate 16, delimits a space corresponding exactly to the gel plate 26 to be made and which is open solely at the end of the frame 10 opposite to the end which is closed by the comb 20 carried by the bottom plate 16. It is through this open end that the gel in liquid form will be poured into the space, until it completely fills it, by means of the device shown in FIGS. 4 and 5.

This pouring device essentially comprises a support plate 52 adapted to be engaged substantially sealed in the open end of the frame 10 between the bottom plate 16 and the membrane 28, the front, transverse edge 54 of this support plate including a top rib 56 forming an abutment on which the membrane 28 is applied. The pouring device further comprises a vertical tank 58 substantially in the form of a funnel, having a cylindrical bottom part 60 engaged with very small clearance in a cylindrical seat 62 with a closed bottom in the support plate, such that the bottom part 60 of the tank can rotate in this seat about a vertical axis. A radial groove 64 is formed in the bottom face of the cylindrical bottom part 60 of the tank, in order to put the interior of the tank into communication with the cylindrical seat 62 formed in the support plate 52. A longitudinal duct 66 is formed in the support plate 52 in order to provide communication between the cylindrical seat 62 and the front transverse edge 54 of the support plate.

The bottom part 60 of the tank 58 is held in the cylindrical seat 62 of the support plate by a bayonet connection, by means of two diametrically opposite recesses 68 formed in the periphery of the bottom part 60 of the tank and two fingers 70 fixed in alignment on the top face of the support plate 52, on either side of the axis of the cylindrical seat 62, the facing ends of the fingers 70 extending above and towards the interior of the cylindrical seat 62 by amounts less than the dimensions of the recesses 68 in the bottom part of the tank.

This pouring device is used in the following manner:

The tank is firstly mounted on the support plate 52, its cylindrical bottom part 60 being fitted in the cylindrical seat 62 with the recesses 68 aligned with the ends of the fingers 70; the bottom part 60 of the tank is then rotated in the cylindrical seat 62 so that the ends of the fingers 70 bear resiliently on the top face of the bottom part 60 of the tank and hold it firmly in the cylindrical seat 62. Notches 72, 74 are advantageously formed in the top face of the bottom part 60, in order to receive projections of corresponding shape provided at the ends of the fingers 70 and accurately determining two angular positions of the tank 58 about its axis, the first angular position defined by the notches 72 being such that the groove 64 is not aligned with the duct 66 and is closed by the wall of the cylindrical seat 62, and the second angular position defined by the notches 74 being such that the groove 64 is aligned with the duct 66, so as to allow the liquid gel contained in the tank 58 to flow into the cassette.

Figure 4:
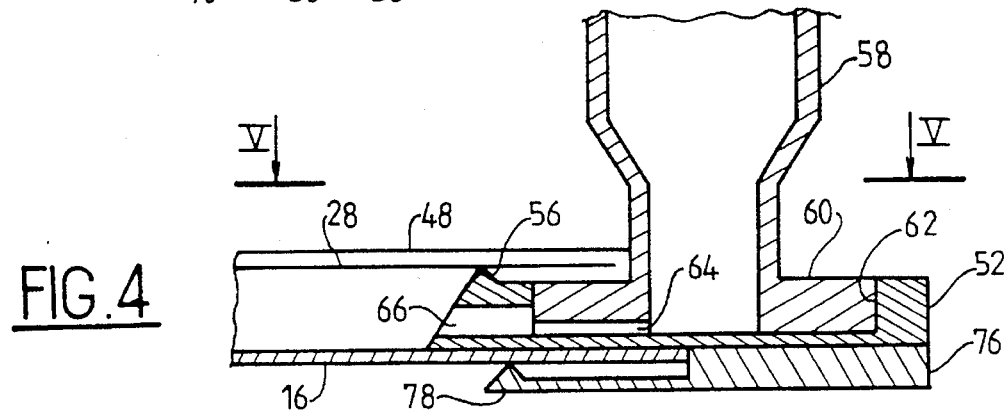
FIG. 4 is a fragmentary view in longitudinal section of means for pouring the gel.
Figure 5:
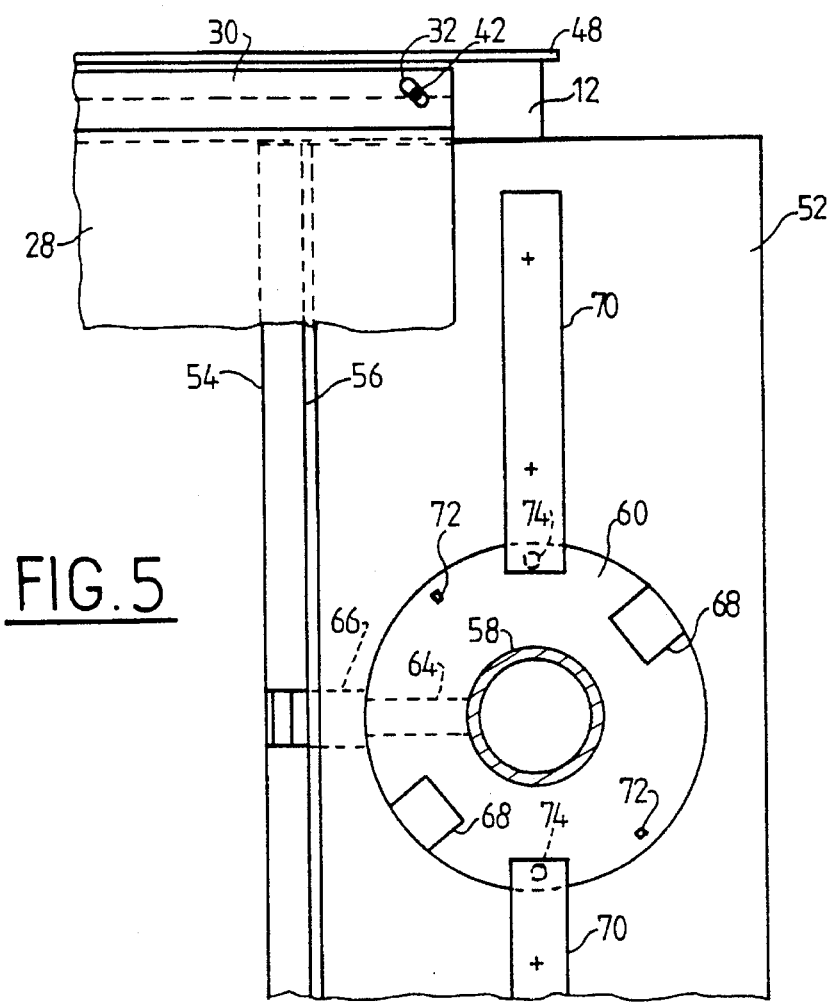
FIG. 5 is a diagrammatic view partially in section along the line V—V of FIG. 4.

When the tank 58 has been thus mounted on the bottom plate 52 and placed in the angular position defined by the notches 72 in which the groove 64 is closed, the support plate 52 is mounted in the open end of the cassette, as shown in FIGS. 4 and 5.

A plate 76 having resiliently deformable longitudinal fingers 78 can advantageously be fixed under the support plate 52, so that the fingers 78 are applied resiliently to the lower face of the bottom plate 16, in order to keep the pouring device in position on the cassette.

The membrane 28 can be mounted on the frame 10 before or after mounting the pouring device on the frame.

When the assembly of the cassette and pouring device is placed on a horizontal support surface, the end of the cassette with the pouring device is slightly higher than the opposite end with the comb 20, on account of the presence of the retaining plate 76, which creates a slight gradient falling towards the comb 20.

A measured amount of liquid gel, (agarose or polyacrylamide for example) is poured into the tank 58 and fills the groove 64, expelling the air contained in this groove through the small clearance between the periphery of the bottom part 60 and the cylindrical wall of the seat 62, this clearance having a value in the order of 0.01 mm for example, which allows the air to escape while preventing passage of the liquid gel.

It is then sufficient to rotate the tank 58 about its axis and place it in the second angular position defined by the notches 74, so that the liquid gel can flow from the tank to the interior of the cassette, passing through the groove 64 and the duct 66.

The liquid gel progressively fills the space defined in the frame 10 between the bottom plate 16 and the tensioned membrane 28. The air contained in this space is evacuated progressively between the membrane 28 and the rib 56 of the support plate 52. In the course of its impregnation by the liquid gel, the membrane 28 tends to elongate and this elongation is automatically taken up as it occurs by the tensioning means formed by the pushers 36 and the associated springs 40.

When the liquid gel has filled the space defined by the frame 10 between the bottom plate 16 and the tensioned membrane 28, it rises to the front transverse edge 54 of the support plate 52, this front edge 54 being beveled to facilitate evacuation of the air and it comes up level with the rib 56 against which the gel-softened membrane 28 is applied. Pouring of the gel is then stopped if there is any remaining in the tank 58, by rotating the tank to place it in its first angular position defined by the notches 72, and the gel is allowed to harden by cooling to ambient temperature (agarose gel) or by polymerization (polyacrylamide gel).

When the gel has solidified, the pouring device is withdrawn from the end of the cassette in which it was engaged.

To use the gel plate covered with the membrane, the assembly of the frame 10, gel plate 26 and membrane 28 is placed vertically in an electrophoresis vessel, the bottom plate 16 is withdrawn and samples of macromolecules are put into the wells 24 of the gel plate.

It will be understood that the method and the apparatus of the invention enable non-specialist personnel to make a gel plate with a microporous membrane rapidly, with a very good quality and perfectly reproducibly.

Figure 6:
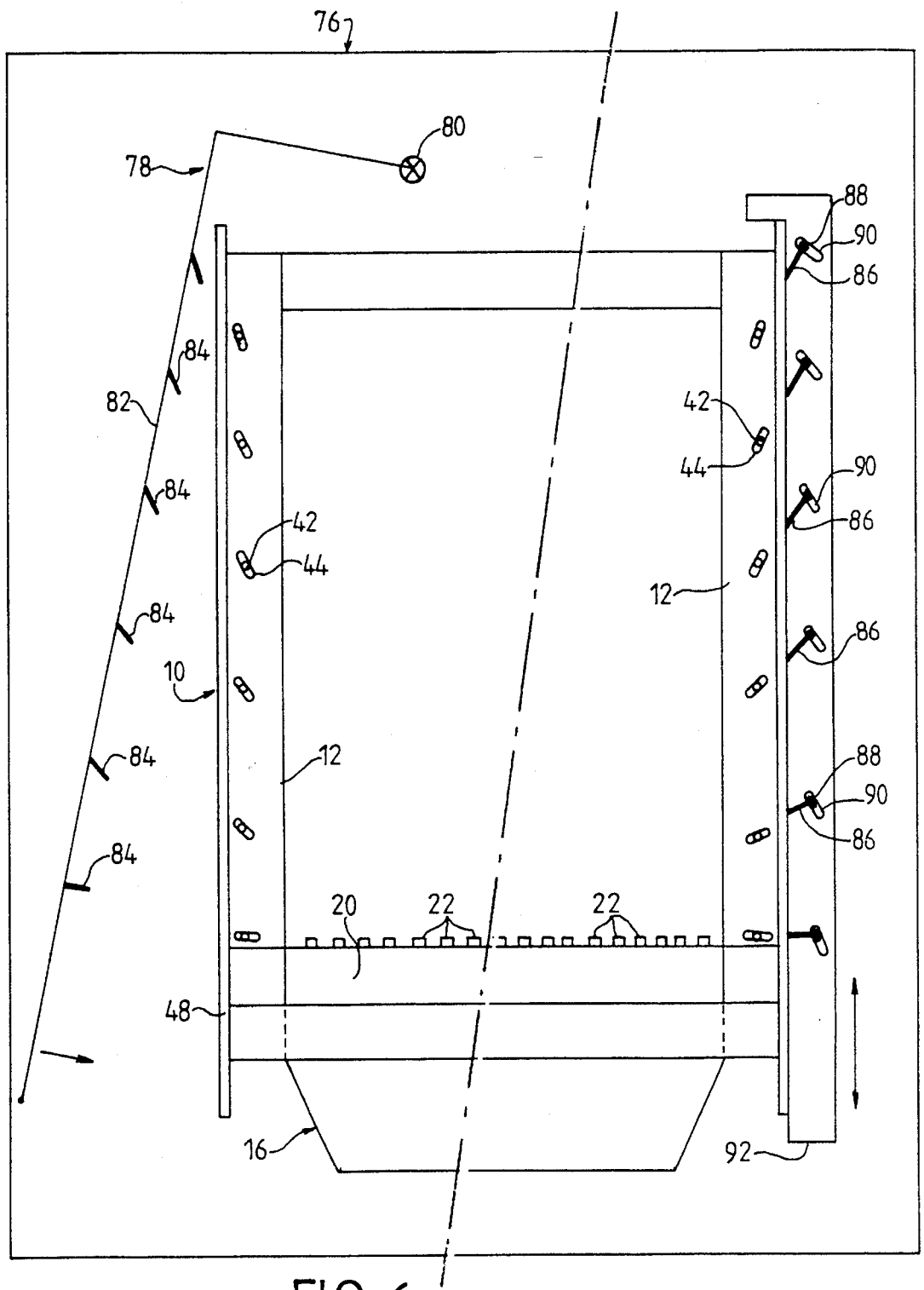
FIG. 6 shows diagrammatically two embodiments of the means used to place a membrane on a cassette.

This manufacture can be further facilitated by use of the tool shown diagrammatically in FIG. 6, which allows simple, rapid and easy fixing of the membrane on the frame 10 of the cassette.

This tool comprises a support table 76 having positioning means (not shown) for the frame 10 fitted with the bottom plate 16. This table 76 is provided with means allowing the tensioning means for the membrane to be pushed back towards the interior of the frame, so that it then suffices to place the membrane fitted with its two strips 30 on top of the frame for the lugs 42 of the tensioning means to engage in the holes 32 in the strips.

These means which allow displacement of the tensioning means, i.e. the pushers 36, towards the interior of the frame, so compressing the associated springs 40, can be of various forms. In the left part of FIG. 6, there is shown a cranked lever 78 pivoted about an axis 80 and whose arm 82 extends alongside one rail 12 of the frame, on the outside thereof, and carries oblique fingers 84 which come into engagement in the guide grooves 38 for the pushers 36 when the lever 78 is swung counterclockwise about the axis 80. The lengths of the fingers 84 are such that, when the arm 82 of the lever is applied to the frame, the lugs 42 of the pushers are automatically placed in a position of engagement in the holes of a strip 30 of a membrane.

As a variant, the means shown in the right part of FIG. 6 can be used, comprising movable fingers 86 guided to move in translation in line with the grooves 38 receiving the pushers 36, these fingers 86 having heads 88 engaged in guide grooves 90 of a slider 92 extending alongside the rail 12 of the frame 8. The orientations of the grooves 90 of the slider 92 are such that, when the slider is shifted in one direction along the rail 12, the fingers 86 are introduced into the guide grooves 38 of the pushers 36 and shift them towards the interior of the frame and, when the slider 92 is shifted in the opposite direction, the fingers 86 are withdrawn from the guide grooves 38 of the pushers 36.

I claim:

1. Apparatus for making a gel plate with a microporous membrane for separation and transfer of macromolecules by electrophoresis, the apparatus comprising a cassette formed by a rectangular frame and a bottom plate, and pouring means for pouring liquid gel into the interior of the cassette onto the bottom plate, said cassette comprising two opposite longitudinal rails having traction means which cooperate with two opposite longitudinal edges of the membrane for placing the latter under tension in substantially uniform manner, before pouring in the gel, and wherein said pouring means are mounted at one end of the cassette and comprise a channel for the gel opening into the cassette between the bottom plate and the membrane tensioned over the cassette, said traction means further comprising pushers guided in grooves in said rails and urged toward the outside by springs, said pushers including means for engaging the edges of the membrane.

2. Apparatus according to claim 1, characterized in that the pushers comprise lugs adapted to be fitted into holes formed in longitudinally extensible strips, which are fixed on the aforesaid edges of the membrane.

3. Apparatus according to claim 1, characterized in that it comprises means acting on the pushers for shifting them towards the interior of the frame, against the action of the springs, into a position allowing a non-tensioned membrane to be placed on the cassette and the engagement of this membrane on the pushers.

4. Apparatus according to claim 3, characterized in that it comprises a support table for positioning the cassette and two movable arms mounted on the table on either side of the cassette and carrying fingers adapted to be engaged in the guide grooves of the pushers, these arms being movable between an active position in which the fingers are engaged in the guide grooves of the pushers and push them towards the interior of the cassette, and an inactive position in which the fingers are retracted from the guide grooves of the pushers.

5. Apparatus according to claim 1, characterized in that the pouring means for the gel comprise a tank carried by a support plate for sealed introduction into one open end of the frame, the tank comprising a cylindrical bottom part mounted to rotate in a cylindrical seat of the support plate and formed with an outlet channel for the gel adapted to be placed by rotation in communication with a duct in the support plate, the ends of the duct opening respectively into the cylindrical housing and the interior of the frame between the bottom plate and the tensioned membrane.

6. Apparatus according to a claim 1, characterized in that the removable bottom plate of the cassette comprises, at one of its ends, a comb for forming wells in the gel plate, this comb closing the end of the frame opposite the end receiving the pouring means in sealed manner.

* * * * *